US012751758B2

(12) United States Patent
Martin et al.

(10) Patent No.: US 12,751,758 B2
(45) Date of Patent: Oct. 6, 2026

(54) CONTROL DEVICE, ELECTROSURGICAL INSTRUMENT AND METHOD FOR CONTROLLING AN ELECTROSURGICAL INSTRUMENT

(71) Applicant: Karl Leibinger Asset Management GmbH & Co. KG, Mühlheim an der Donau (DE)

(72) Inventors: Lukas Martin, Freiburg (DE); Sebastian Herr, Freiburg i. Breisgau (DE)

(73) Assignee: Karl Leibinger Asset Management GmbH & Co. KG, Mühlheim an der Donau (DE)

( * ) Notice: Subject to any disclaimer, the term of this patent is extended or adjusted under 35 U.S.C. 154(b) by 714 days.

(21) Appl. No.: 17/923,305

(22) PCT Filed: May 7, 2021

(86) PCT No.: PCT/EP2021/062225
§ 371 (c)(1),
(2) Date: Nov. 4, 2022

(87) PCT Pub. No.: WO2021/224495
PCT Pub. Date: Nov. 11, 2021

(65) Prior Publication Data
US 2023/0225782 A1 Jul. 20, 2023

(30) Foreign Application Priority Data
May 7, 2020 (DE) ......................... 102020112416.3

(51) Int. Cl.
*A61B 18/12* (2006.01)
*A61B 18/14* (2006.01)
(Continued)

(52) U.S. Cl.
CPC .... *A61B 18/14* (2013.01); *A61B 2017/00203* (2013.01); *A61B 2018/00297* (2013.01);
(Continued)

(58) Field of Classification Search
CPC ............ A61B 18/1442; A61B 18/1445; A61B 18/1447; A61B 2018/00958; A61B 2018/00916; A61B 2018/00952
See application file for complete search history.

(56) References Cited

U.S. PATENT DOCUMENTS 7,628,791 B2 12/2009 Garrison et al.
2003/0055424 A1 3/2003 Ciarrocca
(Continued)

FOREIGN PATENT DOCUMENTS

CN 209301302 U 8/2019
DE 102011082307 3/2013

OTHER PUBLICATIONS

Chinese Office Action (with English translation) for corresponding Application No. 202180033064.X, dated Jul. 9, 2026, 22 pages.

*Primary Examiner* — Sean W Collins
(74) *Attorney, Agent, or Firm* — Dority & Manning, P.A.

(57) ABSTRACT

A control device (1) for an electrosurgical instrument (2), in particular a high-frequency sealing instrument, including a fixed handle part (3), a movable handle part (4), an activation element (5) for activating a current flow, in particular a first type, preferably a sealing current, wherein the activation element (5) is or can be adjusted between a deactivation position and at least one activation position when the movable handle part (4) is actuated, wherein, when the movable handle part (4) is actuated, the activation element (5) is or can be adjusted about an axis of rotation (7).

15 Claims, 5 Drawing Sheets

(51) Int. Cl.
*A61B 17/00* (2006.01)
*A61B 18/00* (2006.01)

(52) U.S. Cl.
CPC ............... *A61B 2018/00607* (2013.01); *A61B 2018/0063* (2013.01); *A61B 2018/0072* (2013.01); *A61B 2018/00928* (2013.01); *A61B 2018/00952* (2013.01); *A61B 2018/00958* (2013.01); *A61B 2018/126* (2013.01)

(56) References Cited

U.S. PATENT DOCUMENTS

| | | | | |
|---|---|---|---|---|
| 2007/0043352 | A1* | 2/2007 | Garrison .............. | A61B 18/085 606/171 |
| 2007/0282333 | A1 | 12/2007 | Fortson et al. | |
| 2011/0077648 | A1* | 3/2011 | Lee .................... | A61B 18/1445 606/51 |
| 2013/0282003 | A1* | 10/2013 | Messerly ........... | A61B 18/1442 606/169 |
| 2013/0304066 | A1* | 11/2013 | Kerr ................... | A61B 18/1445 606/42 |
| 2014/0276736 | A1 | 9/2014 | Worrell et al. | |
| 2015/0005760 | A1* | 1/2015 | Poulsen ............. | A61B 18/1206 606/34 |
| 2016/0175022 | A1 | 6/2016 | Boudreaux et al. | |

* cited by examiner

CONTROL DEVICE, ELECTROSURGICAL INSTRUMENT AND METHOD FOR CONTROLLING AN ELECTROSURGICAL INSTRUMENT

TECHNICAL FIELD

The invention relates to a control device for an electrosurgical instrument and to an electrosurgical instrument, in particular a high-frequency sealing instrument. The electrosurgical instrument can particularly preferably be a bipolar electrosurgical instrument.

BACKGROUND

Control devices for electrosurgical instruments can have at least one switching element for activating a current flow.

Depending on the application, the current flow can be used, for example, for coagulation or for sealing vessels during a surgical procedure.

In what is known as bipolar coagulation, tissue is denatured in order to cause hemostasis. Here, high-frequency alternating current (hereinafter also referred to as HF current) is used to achieve a thermal effect in the tissue. Due to the specific resistance, the electrical energy in the tissue through which electricity flows is converted into thermal energy and thus heats the tissue. Bipolar coagulation is often carried out to stop diffuse bleeding. Hitherto, coagulation has mostly been carried out with bipolar forceps. The tissue is grasped and/or the tips of the forceps are pressed onto the bleeding surface and, by activation via a foot-operated switch or finger switch, the tissue is coagulated for hemostasis.

In what is known as bipolar vessel sealing, vessels, but also tissue layers, are sealed among other things. Vessel sealing is a special form of coagulation. Additional mechanical pressure from the opposing electrodes realigns the collagen and elastin, causing the vessel walls to "fuse" together and become sealed. Instruments for this are mostly bipolar clamps (for open surgery and/or laparoscopy).

Control devices are already known which comprise a fixed handle part and a movable handle part and an activation element for activating a current flow, wherein the activation element is adjustable or adjusted from a deactivation position into at least one activation position when the movable handle part is actuated. This has the advantage that a user, besides applying the force for the adjustment of the handle parts, does not have to additionally and simultaneously activate the current flow, and therefore simplified working is possible. However, previously known control devices for electrosurgical instruments have disadvantages in terms of handling.

Furthermore, previously known instruments are generally tailored to just one field of application, and it may therefore be necessary for a surgeon to have to change instruments during an operation. Not only is a change of instruments disadvantageous for the user on account of the cumbersome handling of the various instruments, the change of instruments also increases the overall operating time. Particularly in situations where quick action is required on the part of the user, a necessary change of instruments may even pose a threat to a patient who is being operated on, for example if bleeding has to be stopped quickly.

SUMMARY

The object is therefore to make available a control device, for an electrosurgical instrument of the type mentioned at the outset, and/or an electrosurgical instrument, in each case with improved usage properties.

According to the invention, the stated object is achieved by a control device having one or more of the features disclosed herein and/or by an electrosurgical instrument having one or more of the features disclosed herein directed to an electrosurgical instrument.

In particular, according to the invention, a control device of the type mentioned at the outset is proposed to achieve the object, wherein the activation element is adjustable or adjusted about a pivot point, in particular about a rotation axis, when the movable handle part is actuated. A particularly reliable and easy activation is thus made possible. Activation of a current flow of a first type, preferably a sealing current, can thereby preferably be provided.

Furthermore, a control device for an electrosurgical instrument is proposed in particular to achieve the object, said control device comprising at least a fixed handle part, a movable handle part, at least one switching element for activating a current flow, wherein the switching element can be actuated by a user independently of an actuation of the movable handle part, the control device being characterized in that the switching element is formed on the movable handle part. It is thus possible for a user to activate a current flow in a simple manner, regardless of whether or not a mechanical pressure is applied to tissue by actuation of the movable handle part. For example, activation of a current flow of a second type, preferably a coagulation current and/or a cutting current, can be made possible. The at least one switching element can be designed as a button, for example. The at least one switching element can preferably be designed as a push button which in particular provides haptic feedback when it is activated. According to a development, it is possible for the control device to have two or more than two switching elements, in particular for activation and/or for switching between at least two bipolar currents.

If the two embodiments described above are thus combined, several fields of application can be covered by one control device and/or one electrosurgical instrument, such that no change of instruments is required. The user can therefore also activate HF current via the at least one switching element, independently of an opening of jaw parts of the electrosurgical instrument, which HF current is used for the bipolar coagulation of tissue. The at least one switching element can in particular activate a switching signal that can be differentiated from bipolar sealing, whereby this is recognized in the generator and the corresponding HF current flows. Since the jaw parts can also be activated in the opened state, the user can use the jaw parts (or the instrument) in the same way as bipolar forceps.

In particular, the object is thus further achieved by a control device, for an electrosurgical instrument, comprising at least one switching element for activating and/or switching a bipolar current flow, characterized in that the at least one switching element enables an activation and/or a switchover between at least two different switching signals, in order to generate at least two different bipolar currents by a generator of the electrosurgical instrument, depending on the respective switching signal. In particular, provision can be made that at least one bipolar coagulation current and/or cutting current and a bipolar sealing current can be activated by the at least two switching signals. Apart from the mechanical pressure on the tissue, the current forms of the generator of an electrosurgical instrument are also decisive for the different applications (such as bipolar coagulation and sealing), which makes it necessary to differentiate the switching signal of both applications in the instrument. The two switching signals can be clearly differentiated, for example, by opposing diodes on the switch/button. The generator recognizes the different activation states and outputs different currents accordingly. In particular, the current in the case of bipolar vessel sealing can be regulated and terminated at the generator side and/or the current in the case of bipolar coagulation can be activated and terminated via the user.

A user therefore no longer has to change instruments during an operation. This greatly simplifies the operation process. In addition, this saves time compared to operations in which a change of instruments is required.

For example, provision can be made that the at least one control element is a switching element that can be directly operated and/or voice-controlled by a user. The at least one switching element can thus be actuated by a user by means of a force applied via a finger and/or a hand. Alternatively or in addition to this, it can be controlled via definable or predefined voice commands, that is to say in particular switching over and/or switching on and/or switching off an HF current.

In the following, further advantageous embodiments of the invention are described which, alone or in combination with the features of other embodiments, can optionally be combined with the features noted above.

According to an advantageous development, the activation element can be designed as a rocker switch. A particularly low-wear and low-maintenance design is thus possible.

According to an advantageous development, provision can be made that an activation element, for example the aforementioned activation element, is formed or arranged on the movable handle part and/or on the fixed handle part. In particular, a rotation axis of the activation element, for example the aforementioned rotation axis of the activation element, can be formed on the movable handle part. It is thus possible to be able to effect the adjustment of the activation element in a simple manner when the movable handle part is actuated relative to the fixed handle part.

To be able to effect a current flow by closing a circuit on the basis of the activation element, provision can be made, according to an advantageous development, that the activation element has at least one contact element, and that the control device has a mating contact surface which is acted upon by the contact element in an activation position. Provision is preferably made here that the contact element is slidably guided along the mating contact surface when the movable handle part is adjusted over an activation section of a total adjustment path of the movable handle part and/or as long as the activation element is in an activation position. Thus, vessel sealing can be achieved only by adjusting the movable handle part relative to the fixed handle part, wherein a mechanical force transmission is initially applied, for example by two opposing and/or closeable branches (also called jaw parts), which are attached for example to a distal end of an end effector and are provided for grasping the tissue that is to be manipulated. A pressure generated on the tissue located between the jaw parts is controlled via the position of the handle parts (and optionally a coupled spring). At a certain, defined position of the handle parts and in particular at a pressure generated thereby on the tissue, the activation element is thus brought into the activation position, which in turn activates the HF current between the jaw parts.

Provision can be made that, in all activation positions of the activation region of the handle part, the contact of the activation element via the contact element with the mating contact element is maintained, as a result of which the HF current remains activated until, for example, the sealing process is recognized as completed either via a generator and/or a control algorithm, or until the user opens the handle parts of the handle and the activation element is deactivated, i.e. until there is no longer any contact between the contact element and the mating contact element. Since the activation of the HF current is controlled via the lever position of the handle and thus the pressure between two jaw parts for example, there is a sufficient process pressure in the branches during vessel sealing.

To be able to effect a current flow by closing a circuit on the basis of the activation element, provision can be made that the contact element and the mating contact surface are conductive. The contact element can in particular have a conductive contact surface. The control device can therefore be designed such that an initially open circuit can be closed by the conductive contact element making contact with the conductive mating contact surface.

In an advantageous development, the activation element can be designed such that a current activated by the activation element flows or can flow through the activation element. The current can be in particular a sealing current, for example the aforementioned sealing current.

For this purpose, provision is preferably made that the activation element has at least one further conductive contact element, for example with a conductive contact surface, and that the at least two conductive contact elements are connected conductively to each other. The further conductive contact element is preferably permanently connected electrically to a conductive mating contact. However, provision can also be made that the mating contact has a mating contact surface with which the further conductive contact element comes into contact during the adjustment of the movable handle part.

The activation element is preferably a conductive component, in particular a conductive rocker switch.

The activation element can be made in particular of metal.

According to an advantageous development, the control device can have at least one reset element which is configured and arranged such that, when the movable handle part is actuated, the activation element is deflectable or deflected from a rest position counter to a restoring force of the at least one reset element. In particular, the reset element can be designed as at least one spring element and/or as at least one magnet. The control device preferably has at least two reset elements that are coupled or can be coupled to the activation element, in particular two reset elements which preferably act in opposition to each other. Provision can further preferably be made that, in the rest position, no force of the at least one reset element acts on the activation element or mutually neutralizing forces of the reset elements act on the activation element.

According to a further advantageous development, the control device can have a guide element made of a non-electrically conductive material, wherein, upon adjustment of the movable handle part from a maximum open position in the direction of a closed position, at least one contact element, for example the aforementioned at least one contact element of the activation element, can be guided via a deactivation section, in particular a first deactivation section, of a or the total adjustment path of the contact element along a first guide surface. In particular, the activation element on the guide element can be deflectable or deflected from its rest position by an angle. Alternatively or in addition to an insulating guide element, provision can be made, according to a further advantageous development, that an air space is used as an insulator. The contact element can thus lie within the air space, at least over a partial region of the deactivation section, such that no current flow is possible.

To be able to give a user feedback on the switch position during operation of the control device, provision can be made, according to an advantageous development, that the control device has at least one feedback element with which the user can be given a haptic and/or acoustic feedback when the movable handle part is moved. In particular, feedback can be conveyed to the user when the activation element is adjusted between a deactivation position and an activation position. Thus, based on the feedback, the user can deduce whether a current flow is activated or not, or whether activation and/or deactivation is imminent, without having to look away from an operating site to a display or the like. The control device can preferably have a guide element, for example the aforementioned guide element, wherein the guide element has, in a first guide surface, a change of direction, in particular a depression and/or an elevation, by which the user can be given haptic feedback. The feedback element can thus create a resistance which is to be overcome, i.e. which has to be overcome in order to reach another switching position (e.g. activated or deactivated).

According to an advantageous embodiment of the control device, a mating contact surface, in particular the aforementioned mating contact surface, can be firmly connected to a carrier element. Alternatively or in addition, the carrier element can be firmly connected to the fixed handle part.

According to a further advantageous embodiment of the control device, the mating contact surface can be formed on a stiff mating contact element, in particular wherein the mating contact surface has at least one change of direction, preferably a curve.

According to an advantageous embodiment of the control device, a mating contact surface, in particular the aforementioned mating contact surface, can be formed on an at least partially bendable mating contact element. In particular, the mating contact element can be designed as a resilient sheet metal.

In both cases, the contact element can be guided by the mating contact surface during an activation position and/or can act on the mating contact surface in order to close a circuit.

According to a further embodiment, a or the aforementioned, preferably electrically insulating, feedback element can be arranged in front of the mating contact element, by means of which acoustic and/or haptic feedback can be conveyed to the user. In particular, the feedback element can be designed such that it can be bent and/or displaced by the activation element, preferably wherein the feedback element is designed as a resilient sheet metal.

To be able to set the times of the current flow to a certain position of the handle parts relative to each other, the control device can have a slotted guide for the at least one contact element of the activation element, which slotted guide is configured such that, when the movable handle part is adjusted relative to the fixed handle part, the contact element is adjusted over a first deactivation section of the total adjustment path, that the first deactivation section is followed in the same direction of adjustment by an activation section, in particular with an end stop of the total adjustment path, and that, when the movable handle part is moved back in the opposite direction relative to the fixed handle part, the contact element is adjusted from the activation section into a second deactivation section and/or a rest position.

According to a further advantageous embodiment, the control device can have a safety device between the movable handle part and the fixed handle part, which safety device prevents an activation of a current flow as long as the movable handle part has not been adjusted, relative to the fixed handle part, beyond an end point, in particular an end point that can be perceived haptically and/or acoustically by a user, of a safety section of the total adjustment path, preferably wherein the safety section is designed to be smaller than the first deactivation section of the total adjustment path.

To enable a signal transmission of at least one switching element, arranged on the movable handle part, in a relatively wear-free manner and/or to enable an activation of a current flow only after a partial actuation of the movable handle part, a safety device between the movable handle part and the fixed handle part can have a resilient contact means, in particular a spring-mounted lifting pin, and a mating contact means. Preferably, once an end point of a safety section has been reached, there is a contact closure between the contact means and the mating contact means, and/or wherein the contact closure is maintained upon continued adjustment up to an end stop of the total adjustment path.

According to a preferred development, at least one switching element or the at least one switching element can be formed on the movable and/or on the fixed handle part and/or on a foot-operated switch element. This has the advantage that it can always be easily reached and operated by a user, irrespective of the position of the handle parts.

According to a particularly preferred embodiment, the movable handle part and the activation element can have different rotation axes, in particular spatially spaced apart rotation axes. Thus, a greater relative deflection of the activation element is possible even with a short adjustment distance of the handle part.

According to a further advantageous embodiment, the internal components, in particular the internal electrical components, of at least the movable handle part can be at least partially accommodated within a sealed interior, in particular within an airtight and/or watertight interior, preferably wherein the interior is formed by overmolding of a preform.

The invention further relates to an electrosurgical instrument, in particular a high-frequency sealing instrument, comprising a control device as described and/or claimed herein, wherein the electrosurgical instrument is configured to be switchable, by means of the control device, between two different bipolar currents that can each be generated by a generator of the electrosurgical instrument. In particular, at least one bipolar coagulation current and a bipolar sealing current can be activated by at least two switching signals of the control device. The electrosurgical instrument can have an end effector, which has a mouth geometry with two branches lying opposite each other in the closed state, wherein the open and closed positions of the branches can be controlled via the position of the handle parts. The two branches can have two electrodes which are insulated from each other and through which an HF current flow is possible across a tissue section lying between them. As a result, sealing and/or coagulation and/or cutting of the tissue can take place via the branches.

An HF current within the meaning of the invention can be defined, for example, at a frequency from 200 kHz, preferably from 300 kHz (as in particular by the standard 60601-2-2).

According to a preferred embodiment, provision can be made that an activation duration for a coagulation current and/or a cutting current is theoretically unlimited and/or is defined by the duration of the actuation of the at least one switching element. A user can thus decide, depending on the application and/or the situation, how long to maintain the activation. Thus, there is preferably no automated shutdown of the coagulation current and/or of the cutting current.

Alternatively or in addition to this, provision can be made, according to a further preferred embodiment, that an activation duration for a sealing current is regulated as a function of time. In particular, automatic shutdown takes place regardless of whether the movable handle part and/or the control element are/is actuated after a maximum activation period has been reached. In particular, a presetting of a tissue-specific maximum activation duration can be stored or storable. Furthermore, an impedance measurement can preferably take place at the generator side, wherein the sealing current is deactivated in an automated manner as a function of the measured impedance.

After the activation, the sealing current is automatically switched off after a maximum activation period has been reached, which for example is preset and/or determined as a function of impedance. In this way, it is possible to prevent tissue damage that occurs as a result of activating the current flow for too long. The automatic switch-off can take place, for example, by automatically switching off a switching signal, in particular on the part of the control device and/or at the generator side. A maximum activation duration can be, for example, at least one second and/or at most 15 seconds, preferably at least 2 seconds and/or at most 10 seconds.

According to an advantageous development, provision can thus be made that the electrosurgical instrument has two mutually insulated electrodes, between which a voltage, in particular a voltage that can be generated by a generator of the electrosurgical instrument, can be applied, in particular wherein the electrodes are each formed by free ends of an end effector, preferably of a bipolar forceps and/or a bipolar clamp and/or a sealing instrument, wherein the electrodes can be configured to be applied to a tissue at a distance from each other, so that an electrical circuit is closed via the tissue.

The electrosurgical instrument preferably does not have a neutral electrode and/or is not configured for monopolar use. Rather, provision can be made that the electrosurgical instrument has an active electrode pair which comprises two active electrodes.

Furthermore, the invention can relate to a method for activating and/or switching at least two bipolar currents in an electrosurgical instrument, as described and/or claimed herein, in which method at least one bipolar coagulation current and/or a bipolar sealing current and/or a bipolar cutting current can be activated by at least two switching signals of the control device.

The invention moreover relates to a method for controlling an electrosurgical instrument, preferably as described and/or claimed herein, in particular through the use of a control device, as described and/or claimed herein, wherein a time-dependent activation of a sealing current takes place when a movable handle part is actuated, and a time-independent activation of a coagulation current and/or of a cutting current takes place when at least one switching element is actuated.

BRIEF DESCRIPTION OF THE DRAWINGS

The invention will now be described in more detail on the basis of a number of illustrative embodiments, although it is not restricted to these illustrative embodiments. Further illustrative embodiments arise by combining the features of individual claims or of a plurality of claims amongst themselves and/or with individual features or a plurality of features of the illustrative embodiments.

In the drawing.

DETAILED DESCRIPTION

Figure 1:
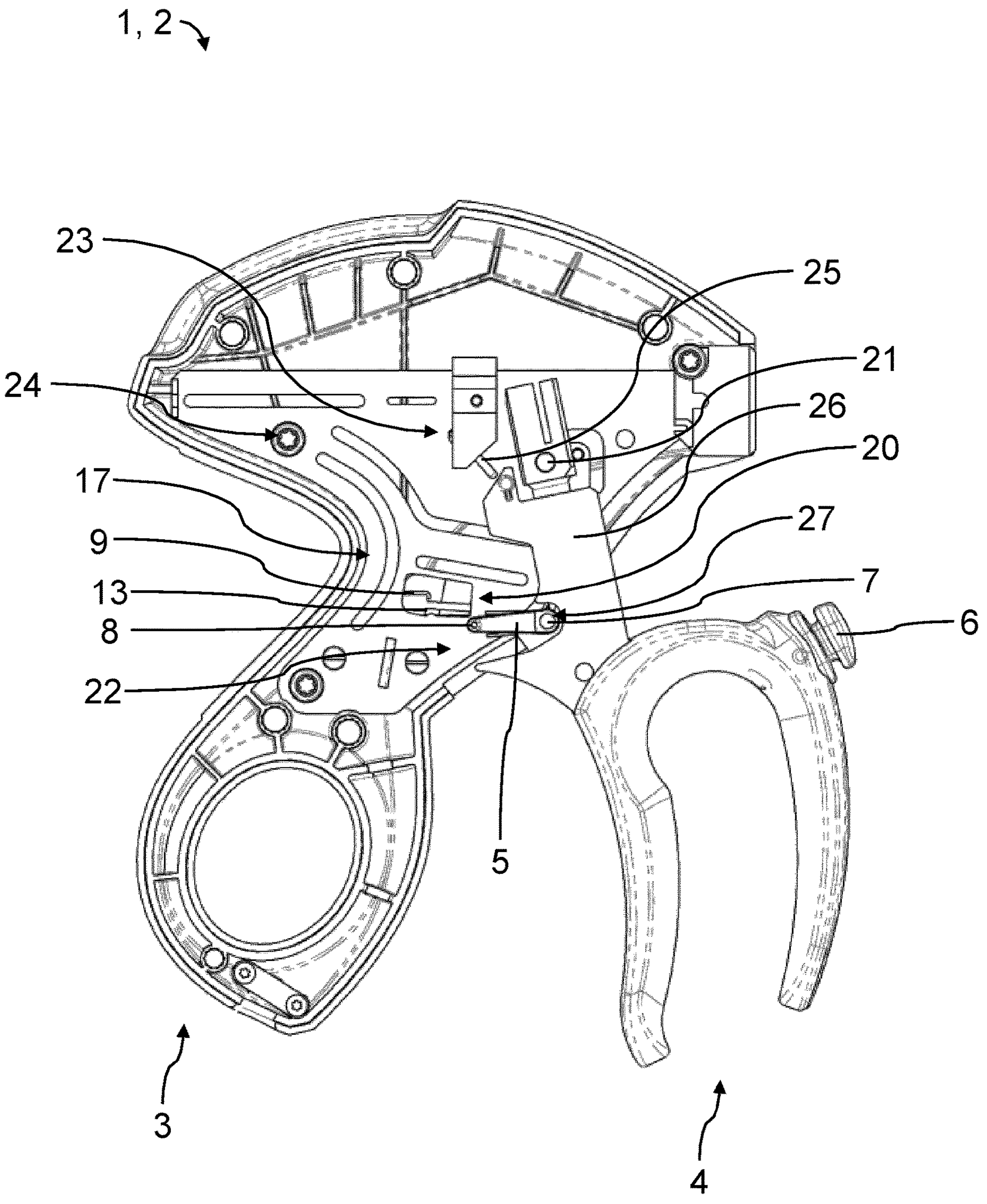
FIG. 1 shows an open side view of a possible embodiment of a control device according to the invention.

FIG. 1 shows a possible embodiment of a control device 1 according to the invention for an electrosurgical instrument 2.

The electrosurgical instrument 2 can be, for example, a high-frequency instrument for generating a plurality of different bipolar currents.

The control device 1 has a handle with a fixed handle part 3, and with a handle part 4 that is movable in particular via a pivot joint. The handle can be held in one hand by a user, and at the same time the movable handle part 4 can be adjusted with this hand relative to the fixed handle part 3.

The movable handle part 4 is in operative connection, in particular mechanical operative connection, with an activation element 5. The activation element 5 is configured to close a circuit and thus activate a flow of a sealing current. This is done by actuating the movable handle part 4 from a deactivation position into at least one activation position, for example into an activation region with a plurality of activation positions.

To form the circuit, the control device 1 has a first power connection 23 and a second power connection 24 of opposite polarity. A current source, in particular a high-frequency current source, can be connected to the power connections 23 and 24. The power connection 24 is formed on the conductive carrier element 17. As is indicated, it can be formed for example on an actuation means or also at another location of the carrier element 17 or of a conductive component part of the control device. The power connection 23 is, as indicated, formed on a conductive contact pin 25, although it can also be formed on another conductive component part of the control device.

The contact pin 25 is insulated from the carrier element 17, so that no direct flow of current can be formed between them. A current can instead flow from the power connection 23 via the contact pin 25, which in a partially retracted position of the movable handle part 4 contacts an electrical conductor formed in the proximal element 26 of the handle part 4, and then via this conductor to the activation element 5. For this purpose, the conductor contacts the activation element 5 at a contact element 27. The contact element 27 can be a conductive surface of the activation element 5 or also a conductive pin or the like. The current then flows through the activation element 5 to the contact element 8 which, as the handle part 4 is pulled further, contacts the mating contact surface 9. The mating contact surface 9 is electrically connected to the carrier element 17, such that a closed circuit can be formed for the sealing current.

Figure 4:
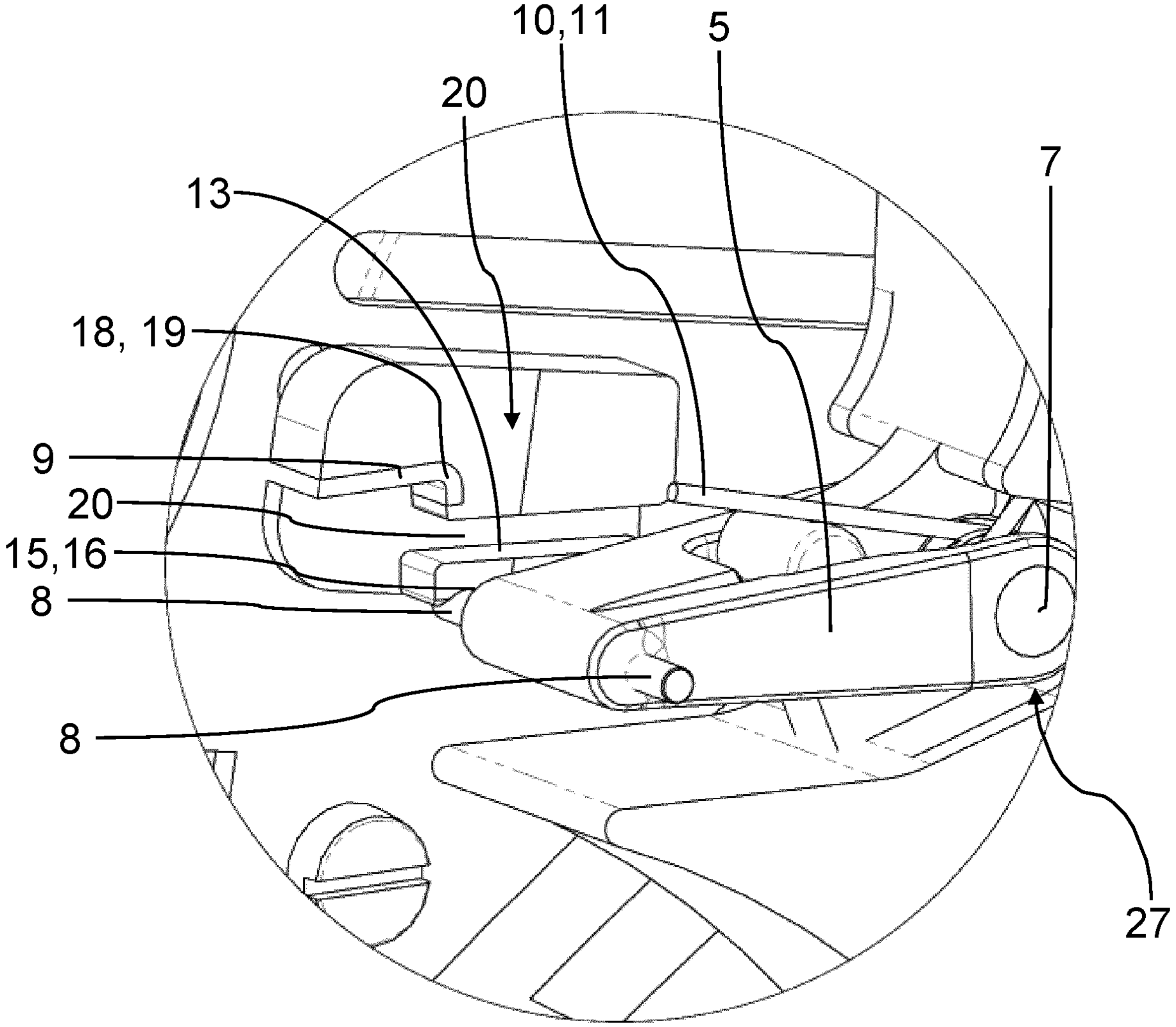
FIG. 4 shows a detailed view of the activation element, configured as a rocker switch, of the variant embodiment of the control device from FIG. 1, wherein a status of a haptic feedback before an automatic activation is shown.
Figure 5:
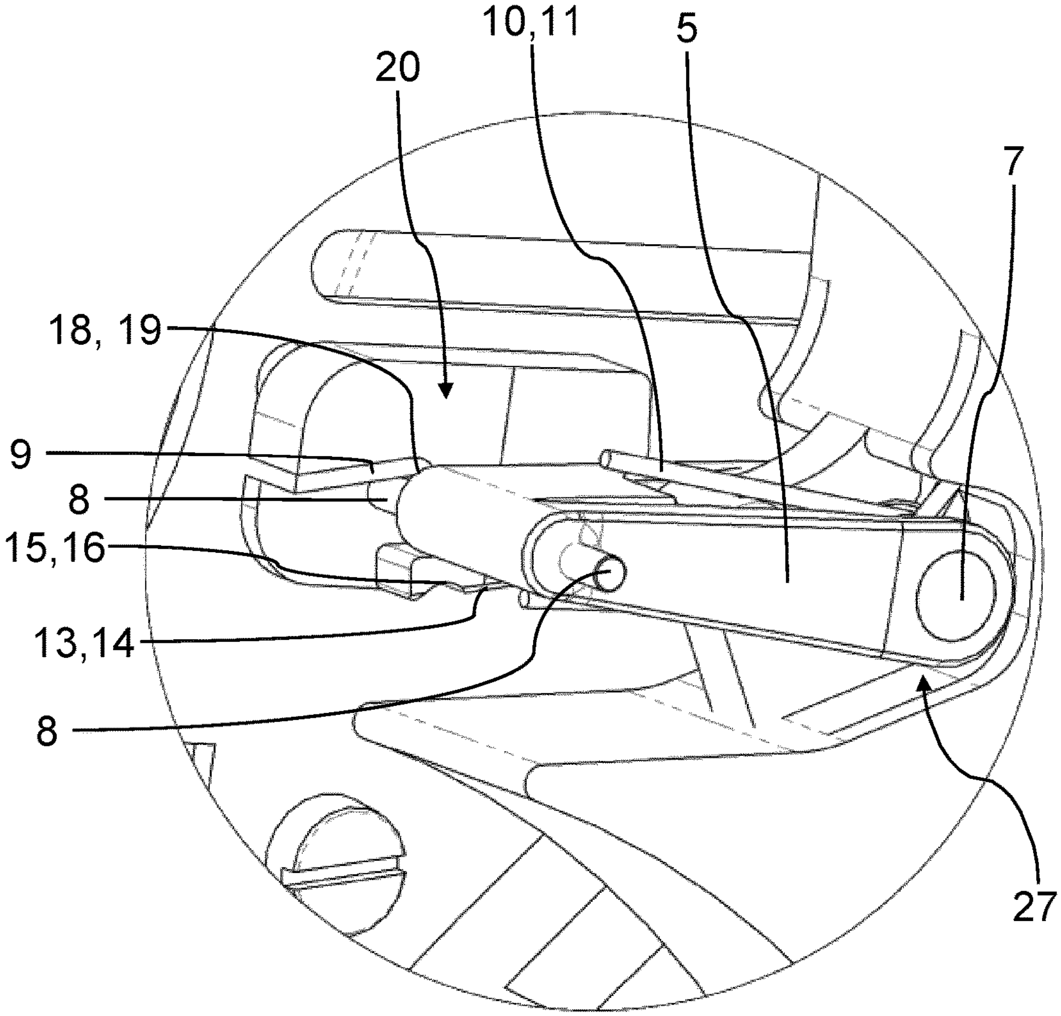
FIG. 5 shows a further detailed view of the activation element of FIG. 4, wherein the activation element is in the status of an automatic activation.
Figure 6:
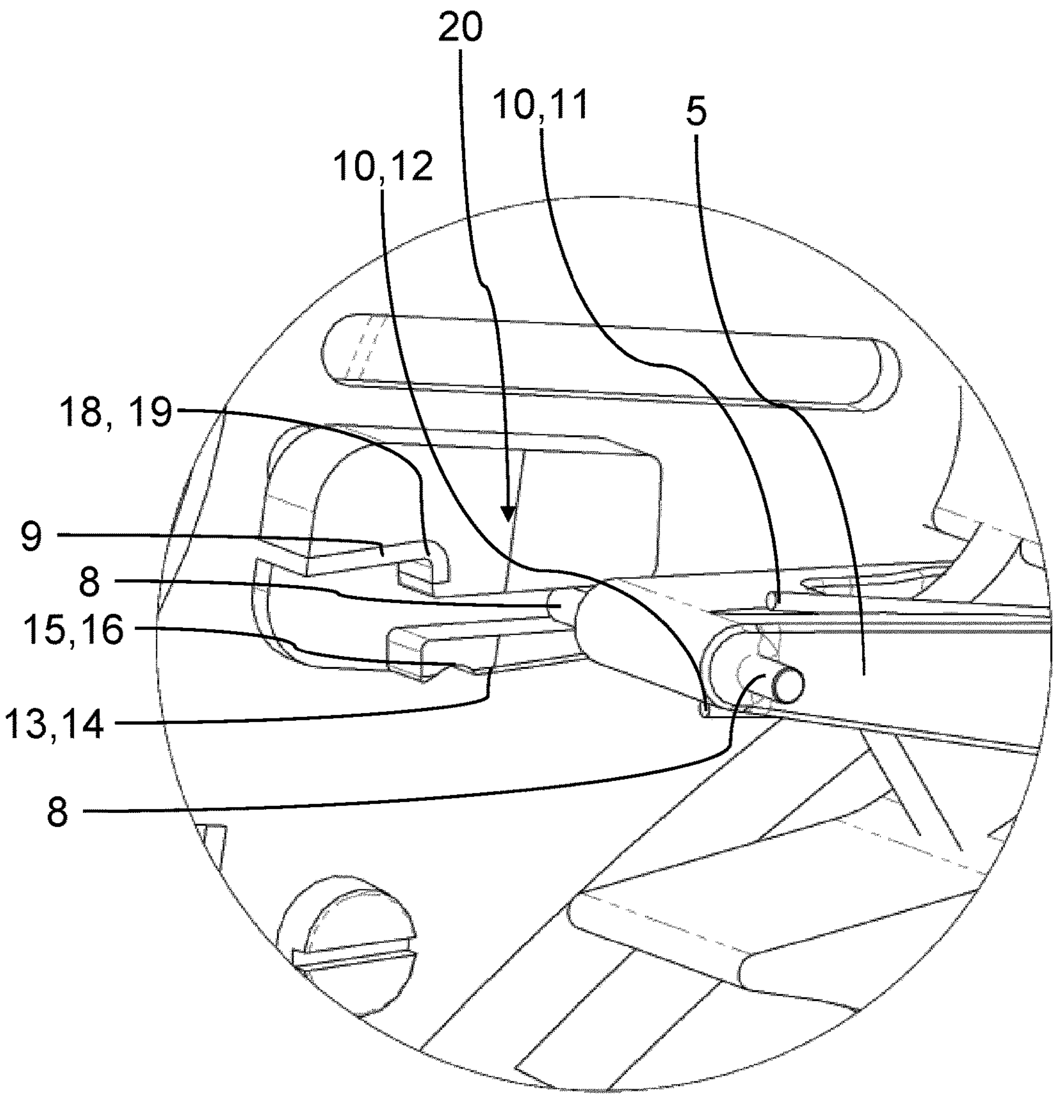
FIG. 6 shows a further detailed view of the activation element from FIGS. 4 and 5, wherein the activation element is in the deactivated status and/or before the lever is extended.

FIGS. 4-6 show an illustrative embodiment of an activation element 5 as a rocker switch, wherein the activation element 5 is provided here to activate a sealing current. The activation element 5 can thus be adjusted about a rotation axis 7 upon actuation of the movable handle part 4.

Figure 2:
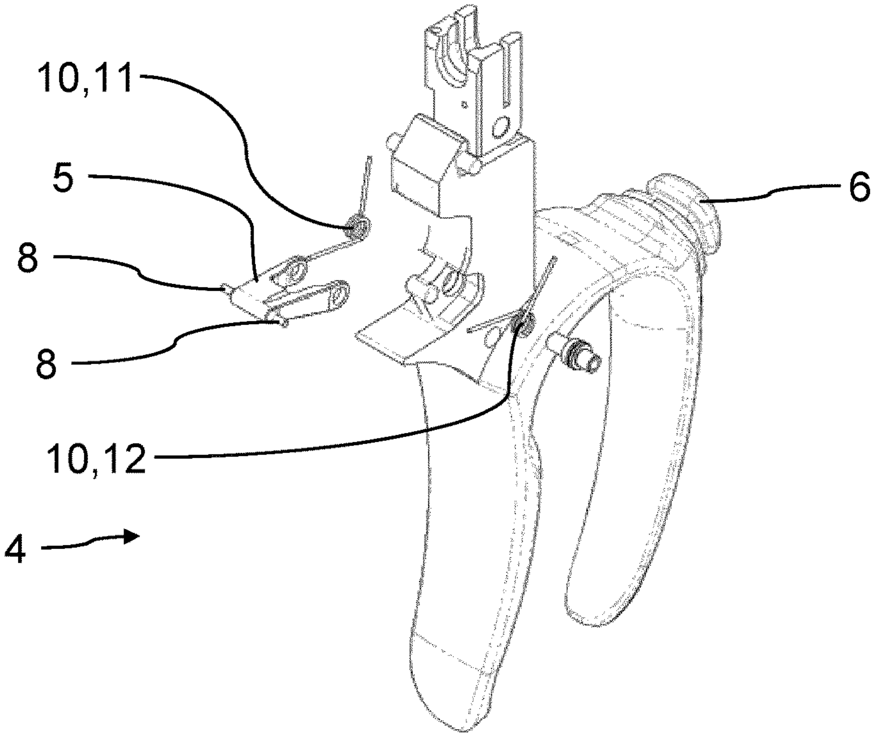
FIG. 2 shows an exploded view of the movable handle part of the control device of FIG. 1.
Figure 3:
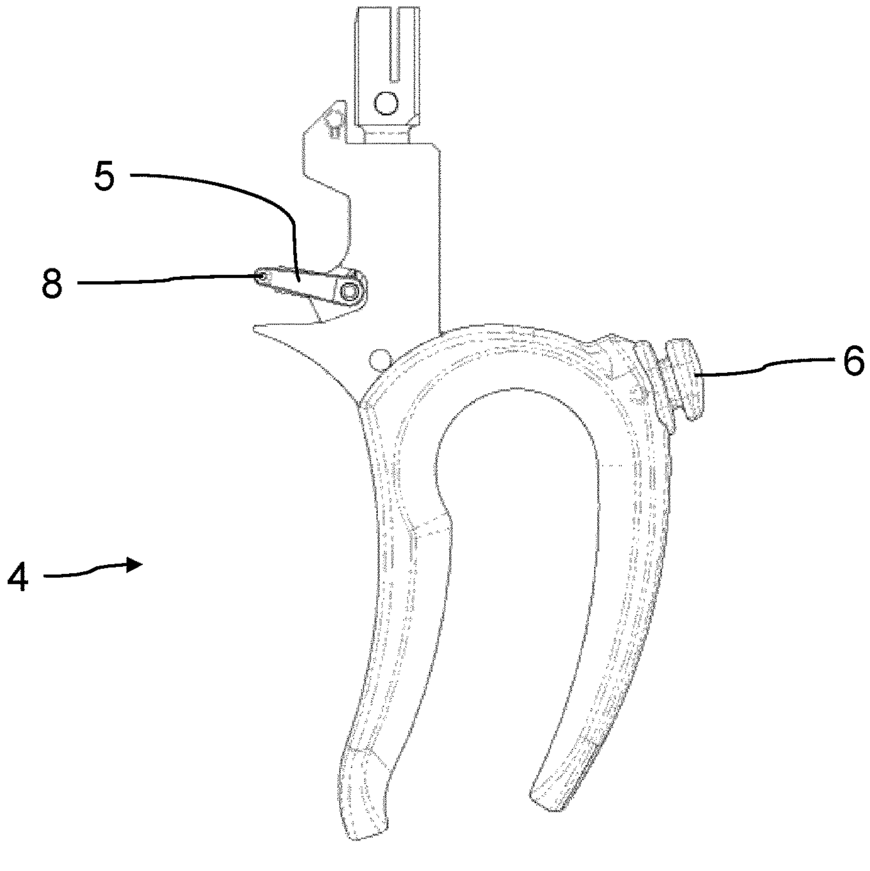
FIG. 3 shows a side view of the assembled movable handle part of FIG. 2.

The control device 1 further comprises at least one switching element 6 for activating a coagulation current and/or a cutting current. As can be seen in FIGS. 1, 2 and 3, the switching element 6 is designed as a push button on the movable handle part 4. A user can thus simultaneously activate a sealing current and a coagulation current and/or a cutting current, preferably independently of one another, with just one hand. For the coagulation current, the same power connections 23 and 24 can be used as are also used for the sealing current. For example, the conductor formed in the proximal element 26 of the handle part 4 can have a bifurcation, wherein the second line is routed to the switching element 6. The switching element 6 can then be in electrical contact with the carrier element 17.

The activation of the switching element 6 is thus effected by pressing, it being possible to do this independently of an actuation of the movable handle part 4.

By actuating the movable handle part 4 and/or actuating the switching element 6, a specific switching signal to a generator of the electrosurgical instrument 2 can be activated in each case, wherein a certain type of high-frequency (HF) current, in particular one of at least two different bipolar currents, for example as mentioned above, is generated as a function of the switching signal.

As is shown in FIGS. 1, 2 and 3, the activation element 5 is arranged about its rotation axis 7 on the movable handle part 4.

On the activation element 5, for example, a contact element 8 with a conductive contact surface is formed at a free end. The fixed handle part 3 and/or a carrier element 17 have/has a mating contact element 9 with a conductive mating contact surface.

In an activation position of the activation element 5, the conductive contact surface and the mating contact surface contact each other. This contact remains upon further adjustment of the movable handle part 4 relative to the fixed handle part 3 over an activation section, that is to say a partial section of a total adjustment path, such that a circuit is closed. The current flows here through the activation element 5. The contact element 8 is guided slidingly along the mating contact surface 9 along the activation section.

The activation element 5 is in operative connection with at least one reset element 10, in particular with two reset elements 10 which preferably act in opposition to each other. When the movable handle part 4 is actuated, the activation element 5 is deflected from a rest position counter to a restoring force of the reset elements 10. In the rest position, no force of the mutually neutralizing force effects of the reset element 10 acts on the activation element 5. As soon as the movable handle part 4 is actuated, the activation element 5 must be adjusted counter to the restoring force of at least one reset element 10. The reset elements 10 can, for example, be designed as a first spring element 11 and a second spring element 12, in particular as leg springs.

To ensure that a user can recognize at least haptically when there is contact between the contact element 8 and the mating contact surface 9, the control device 1 has at least one feedback element 15. By means of the feedback element 15, the user can be given haptic feedback during a movement of the movable handle part 4, when an adjustment of the activation element 5 takes place between a deactivation position and an activation position. The feedback element 15 can, for example, be designed as a depression 16 in a guide surface 14 of a guide element 13.

FIG. 4 shows that, by the actuation of the movable handle part 4, the contact element 8 designed as a pin has been guided along the guide surface 14 of the guide element 13 as far as the feedback element 15 designed as a depression 16, and the contact element 8 engages in the depression 16. To move the contact element 8 out of the depression 16, the user has to overcome a perceptible resistance by applying a slightly increased actuation force. Through the haptic feedback, the user knows that, upon further actuation, he will activate the sealing current, by the contact element 8 being moved from the feedback element 15 to the mating contact element 9.

FIG. 5 shows the contact element 8 in the activation position, as it bears on the mating contact surface of the mating contact element 9, whereby the circuit is closed. Upon further actuation of the movable handle part 4, the contact element 8 is guided along the mating contact surface of the mating contact element 9, and the circuit remains closed over this activation section.

A sealing current can be deactivated in a time-dependent manner by regulation of the generator of the electrosurgical instrument 2. It is particularly advantageous if an impedance measurement is carried out, with a time-dependent deactivation of the sealing current taking place at the generator when a certain impedance value is reached, in particular exceeded or not reached.

The sealing current can also be deactivated by returning the movable handle part 4 to its rest position, by the contact element 8 being moved away from the mating contact element 9 so that the circuit is opened. The resetting of the movable handle part 4 from the activation position into the deactivation position is shown in FIG. 6. There is therefore no contact here between the contact element 8 and the mating contact element 9.

As can be seen from FIGS. 4-6, the mating contact element 9 can be designed, for example, as a contact plate.

LIST OF REFERENCE SIGNS

1 control device for an electrosurgical instrument
2 electrosurgical instrument
3 fixed handle part
4 movable handle part
5 activation element (here e.g. rocker switch)
6 switching element
7 rotation axis of the activation element
8 contact element of the activation element
9 mating contact element (here e.g. contact plate)
10 reset element
11 first spring element
12 second spring element
13 guide element
14 guide surface
15 feedback element
16 depression
17 carrier element
18 change of direction
19 curve
20 slotted guide
21 rotation axis of the movable handle part
22 safety device
23 power connection

24 further power connection contact pin
26 element of 4
27 contact element

The invention claimed is:

1. A control device (1) for an electrosurgical instrument (2), the control device comprising:
a fixed handle part (3);
a movable handle part (4); and
an activation element (5) configured to activate a current flow, wherein the activation element (5) is adjustable or adjusted about a pivot point from a deactivation position into at least one activation position through actuation of the movable handle part (4), wherein the movable handle part (4) is in mechanical operative connection with the activation element (5), and the activation element is configured such that a current activated by the activation element flows or is adapted to flow through the activation element.

2. The control device (1) as claimed in claim 1, wherein the activation element (5) is formed or arranged on the movable handle part (4) or on the fixed handle part (3).

3. The control device (1) as claimed in claim 1, wherein the activation element (5) has at least one conductive contact element (8, 27), and the control device (1) has a conductive mating contact surface (9) which, in an activation position, is acted upon by the contact element (8, 27).

4. The control device (1) as claimed in claim 1, wherein the control device (1) has at least one reset element (10), and when the movable handle part (4) is actuated, the activation element (5) is deflectable or deflected from a rest position counter to a restoring force of the at least one reset element (10).

5. The control device (1) as claimed in claim 1, wherein the control device (1) has at least one feedback element (15) with which at least one of a haptic or acoustic feedback is provided to a user when the movable handle part (4) is moved.

6. The control device (1) as claimed in claim 1, wherein the current flow is of a first type.

7. The control device (1) as claimed in claim 6, further comprising at least one switching element (6) for activating a current flow of a second type, the at least one switching element (6) is formed on the movable handle part (4), and the at least one switching element (6) is actuatable by a user independently of an actuation of the movable handle part (4).

8. The control device (1) as claimed in claim 4, wherein, in a rest position, no force of the at least one reset element (10) acts on the activation element (5) or mutually neutralizing forces of the at least one reset element (10) act on the activation element (5).

9. A control device (1) for an electrosurgical instrument (2), the control device comprising:
at least a fixed handle part (3);
a movable handle part (4);
an activation element (5) configured to activate a current flow of a first type, wherein the activation element (5) is adjustable or adjusted from a deactivation position into at least one activation position through actuation of the movable handle part (4), and the movable handle part (4) is in mechanical operative connection with the activation element (5); and
at least one switching element (6) for activating a current flow of a second type, the at least one switching element (6) is formed on the movable handle part (4), and the at least one switching element (6) is actuatable by a user independently of an actuation of the movable handle part (4).

10. The control device (1) as claimed in claim 9, wherein:
the at least one switching element (6) is configured for at least one of activating or switching a bipolar current flow, the at least one switching element (6) enables at least one of an activation or a switchover between at least two different switching signals, in order to generate at least two different bipolar currents by a generator of the electrosurgical instrument (2) depending on the respective switching signal, wherein the switching element (6) is configured to either have an activated state or an inactivated state, and a distinction between the at least two different switching signals is based on the activated state of the switching element (6) and a signal of an activation element (5).

11. The control device (1) as claimed in claim 9, wherein at least one or the at least one switching element (6) is formed on the movable handle part (4), the fixed handle part (3), or on a foot-operated switch element.

12. An electrosurgical instrument (2), comprising a control device (1) as claimed in claim 10, wherein the electrosurgical instrument (2) is configured to be switchable, by the control device (1), between two different bipolar currents that are generated by a generator of the electrosurgical instrument (2), and at least one bipolar coagulation current as the current of the second type and a bipolar sealing current as the current of the first type are activatable by at least two switching signals of the control device (1).

13. The control device (1) as claimed in claim 10, wherein the switching element (6) is configured to be at least one of directly operated or voice-controlled by a user.

14. The control device (1) as claimed in claim 10, wherein at least one of a bipolar coagulation current or a bipolar cutting current and a bipolar sealing current are activatable by the at least two switching signals.

15. A control device (1) for an electrosurgical instrument (2), the control device comprising:
a fixed handle part (3);
a movable handle part (4);
an activation element (5) configured to activate a current flow, the activation element (5) is adjustable or adjusted about a pivot point from a deactivation position into at least one activation position when the movable handle part (4) is actuated, and the activation element is configured such that a current activated by the activation element flows or is adapted to flow through the activation element, wherein the activation element (5) has at least one conductive contact element (8, 27), and the control device (1) has a conductive mating contact surface (9) which, in an activation position, is acted upon by the contact element (8, 27); and
wherein at least one of during an adjustment of the movable handle part (4) over an activation section of a total adjustment path of the movable handle part (4) or as long as the activation element (5) is in the activation position, the contact element (8, 27) is guided slidingly along the mating contact surface (9).

* * * * *